(12) United States Patent
Nattinger et al.

(10) Patent No.: US 12,315,034 B2
(45) Date of Patent: May 27, 2025

(54) CAPTURING AND STORING AN IMAGE OF A PHYSICAL ENVIRONMENT

(71) Applicant: Apple Inc., Cupertino, CA (US)

(72) Inventors: Elena J. Nattinger, Menlo Park, CA (US); Peter Burgner, Sunnyvale, CA (US); Anna L. Brewer, Cupertino, CA (US); Devin W. Chalmers, Oakland, CA (US)

(73) Assignee: APPLE INC., Cupertino, CA (US)

( * ) Notice: Subject to any disclaimer, the term of this patent is extended or adjusted under 35 U.S.C. 154(b) by 263 days.

(21) Appl. No.: 18/196,241

(22) Filed: May 11, 2023

(65) Prior Publication Data

US 2023/0368327 A1    Nov. 16, 2023

Related U.S. Application Data

(60) Provisional application No. 63/341,193, filed on May 12, 2022.

(51) Int. Cl.
| | |
|---|---|
| *G06T 1/60* | (2006.01) |
| *A61B 5/024* | (2006.01) |
| *G06F 3/01* | (2006.01) |
| *G06V 10/74* | (2022.01) |
| *G06V 40/16* | (2022.01) |

(52) U.S. Cl.
CPC ............ *G06T 1/60* (2013.01); *A61B 5/024* (2013.01); *G06F 3/013* (2013.01); *G06V 10/761* (2022.01); *G06V 40/174* (2022.01)

(58) Field of Classification Search
CPC .................................................... G06T 1/60
See application file for complete search history.

(56) References Cited

U.S. PATENT DOCUMENTS

| | | | |
|---|---|---|---|
| 2014/0298386 A1* | 10/2014 | Dasgupta ........... | H04N 21/4532 725/46 |
| 2020/0082576 A1* | 3/2020 | Lai ..................... | G06F 3/011 |
| 2022/0139052 A1* | 5/2022 | Tavakoli ............. | G06T 19/006 345/633 |
| 2023/0107108 A1* | 4/2023 | Aravamudan ...... | H04N 21/41407 382/312 |

* cited by examiner

*Primary Examiner* — Shivang I Patel
(74) *Attorney, Agent, or Firm* — Fernando & Partners, LLP

(57) ABSTRACT

A method includes, while presenting a representation of a physical environment of the device, obtaining contextual data that indicates a characteristic of the physical environment, the device or a user of the device, and obtaining an indication of historical content associated with the device. The method includes determining, based on the characteristic indicated by the contextual data and the historical content, a user interest value that indicates a user interest level in the physical environment. The method includes storing an image captured by an image sensor in response to the user interest value being greater than a threshold interest value.

20 Claims, 8 Drawing Sheets

US 12,315,034 B2

CAPTURING AND STORING AN IMAGE OF A PHYSICAL ENVIRONMENT

CROSS-REFERENCE TO RELATED APPLICATIONS

This application claims the benefit of U.S. Provisional Patent App. No. 63/341,193, filed on May 12, 2022, which is incorporated by reference in its entirety.

TECHNICAL FIELD

The present disclosure generally relates to capturing and storing an image of a physical environment.

BACKGROUND

Some devices include an image sensor such as a camera. A user can provide a user input to trigger the camera to capture an image of a physical environment. For example, some devices may include a camera application that can present a user interface that includes a capture button that the user can select to trigger the camera to capture an image of the physical environment. Navigating to the user interface of the camera application and capturing the image may require the user to provide a sequence of user inputs.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

Figure 1A:
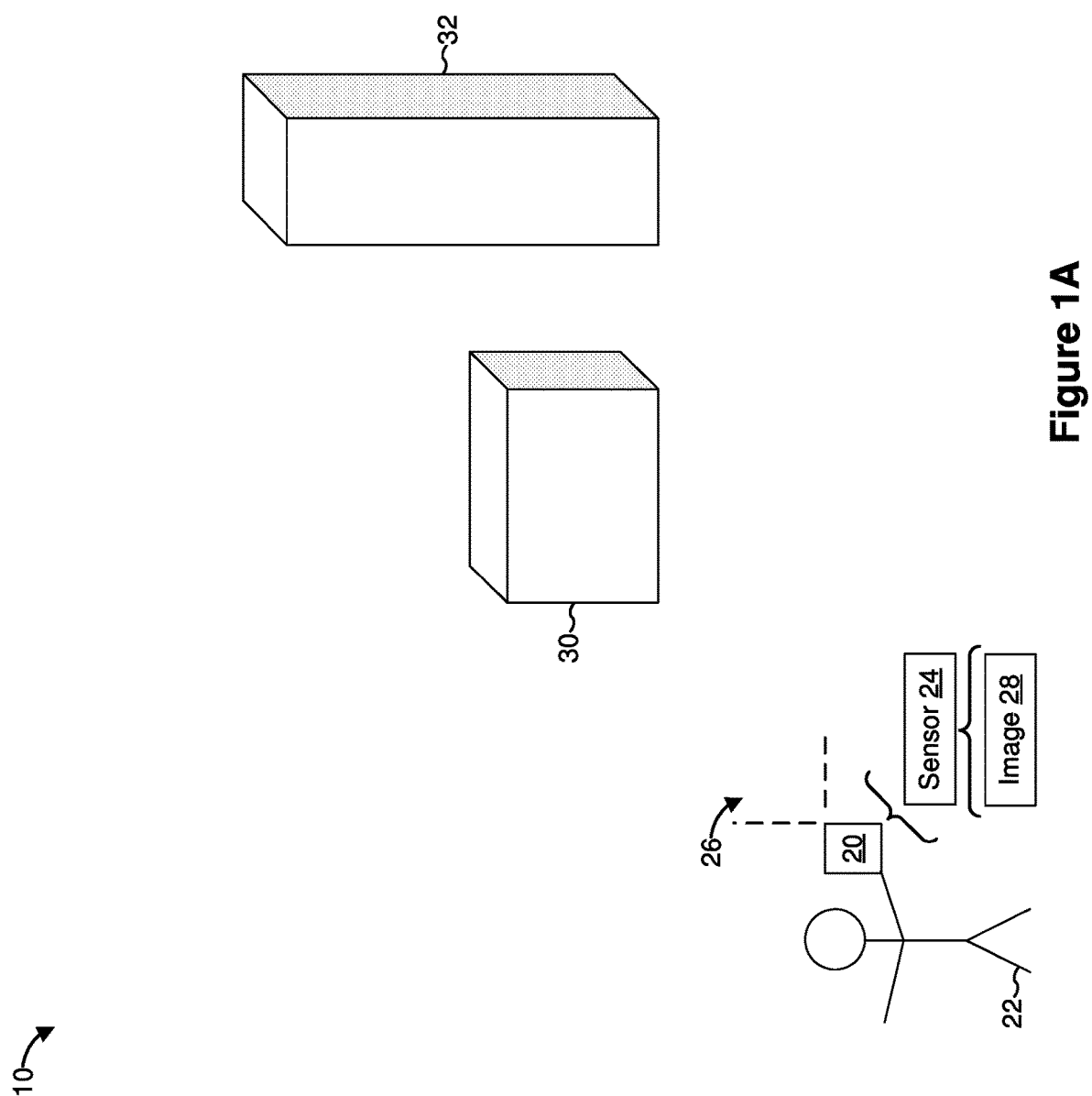
FIGS. 1A-1E are diagrams of an example operating environment in accordance with some implementations.

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

SUMMARY

Various implementations disclosed herein include devices, systems, and methods for capturing and storing an image of a physical environment based on user interest. In some implementations, a device includes a display, an image sensor, a non-transitory memory, and one or more processors coupled with the display, the image sensor and the non-transitory memory. In various implementations, a method includes, while presenting a representation of a physical environment of the device, obtaining contextual data that indicates a characteristic of the physical environment, the device or a user of the device, and obtaining an indication of historical content associated with the device. In some implementations, the method includes determining, based on the characteristic indicated by the contextual data and the historical content, a user interest value that indicates a user interest level in the physical environment. In some implementations, the method includes storing an image captured by the image sensor in response to the user interest value being greater than a threshold interest value.

In accordance with some implementations, a device includes one or more processors, a non-transitory memory, and one or more programs. In some implementations, the one or more programs are stored in the non-transitory memory and are executed by the one or more processors. In some implementations, the one or more programs include instructions for performing or causing performance of any of the methods described herein. In accordance with some implementations, a non-transitory computer readable storage medium has stored therein instructions that, when executed by one or more processors of a device, cause the device to perform or cause performance of any of the methods described herein. In accordance with some implementations, a device includes one or more processors, a non-transitory memory, and means for performing or causing performance of any of the methods described herein.

DESCRIPTION

Numerous details are described in order to provide a thorough understanding of the example implementations shown in the drawings. However, the drawings merely show some example aspects of the present disclosure and are therefore not to be considered limiting. Those of ordinary skill in the art will appreciate that other effective aspects and/or variants do not include all of the specific details described herein. Moreover, well-known systems, methods, components, devices and circuits have not been described in exhaustive detail so as not to obscure more pertinent aspects of the example implementations described herein.

A physical environment refers to a physical world that people can sense and/or interact with without aid of electronic devices. The physical environment may include physical features such as a physical surface or a physical object. For example, the physical environment corresponds to a physical park that includes physical trees, physical buildings, and physical people. People can directly sense and/or interact with the physical environment such as through sight, touch, hearing, taste, and smell. In contrast, an extended reality (XR) environment refers to a wholly or partially simulated environment that people sense and/or interact with via an electronic device. For example, the XR environment may include augmented reality (AR) content, mixed reality (MR) content, virtual reality (VR) content, and/or the like. With an XR system, a subset of a person's physical motions, or representations thereof, are tracked, and, in response, one or more characteristics of one or more virtual objects simulated in the XR environment are adjusted in a manner that comports with at least one law of physics. As one example, the XR system may detect head movement and, in response, adjust graphical content and an acoustic field presented to the person in a manner similar to how such views and sounds would change in a physical environment. As another example, the XR system may detect movement of the electronic device presenting the XR environment (e.g., a mobile phone, a tablet, a laptop, or the like) and, in response, adjust graphical content and an acoustic field presented to the person in a manner similar to how such views and sounds would change in a physical environment.

In some situations (e.g., for accessibility reasons), the XR system may adjust characteristic(s) of graphical content in the XR environment in response to representations of physical motions (e.g., vocal commands).

There are many different types of electronic systems that enable a person to sense and/or interact with various XR environments. Examples include head mountable systems, projection-based systems, heads-up displays (HUDs), vehicle windshields having integrated display capability, windows having integrated display capability, displays formed as lenses designed to be placed on a person's eyes (e.g., similar to contact lenses), headphones/earphones, speaker arrays, input systems (e.g., wearable or handheld controllers with or without haptic feedback), smartphones, tablets, and desktop/laptop computers. A head mountable system may have one or more speaker(s) and an integrated opaque display. Alternatively, a head mountable system may be configured to accept an external opaque display (e.g., a smartphone). The head mountable system may incorporate one or more imaging sensors to capture images or video of the physical environment, and/or one or more microphones to capture audio of the physical environment. Rather than an opaque display, a head mountable system may have a transparent or translucent display. The transparent or translucent display may have a medium through which light representative of images is directed to a person's eyes. The display may utilize digital light projection, OLEDs, LEDs, uLEDs, liquid crystal on silicon, laser scanning light source, or any combination of these technologies. The medium may be an optical waveguide, a hologram medium, an optical combiner, an optical reflector, or any combination thereof. In some implementations, the transparent or translucent display may be configured to become opaque selectively. Projection-based systems may employ retinal projection technology that projects graphical images onto a person's retina. Projection systems also may be configured to project virtual objects into the physical environment, for example, as a hologram or on a physical surface.

Some devices include a camera that can capture pictures or record videos. Most devices include a camera application that allows a user of the device to control the camera. The camera application generates and presents a graphical user interface (GUI) that allows the user to capture an image or record a video. The GUI may include a capture button that the user can press in order to capture an image or record a video. Sometimes capturing an image of an object or an environment that interests the user is difficult because the user may not be able to launch the camera interface in time or the user's hands may be occupied. Continuously capturing images may not be feasible due to limitations on power consumption and/or memory usage.

The present disclosure provides methods, systems, and/or devices for automatically capturing and storing an image based on user interest. The device determines whether or not the user may be interested in capturing an image of a physical environment of the device or of a particular physical article in the physical environment. If the device determines that the user may be interested in capturing an image, the device automatically captures and stores the image. Automatically storing and capturing the image reduces the need for the user to navigate to the camera application and press the capture button to capture the image. As such, the device may be able to capture images that the user may not be able to capture due to the delay in navigating to the camera application and pressing the capture button.

The device can determine whether the user is interested in capturing and storing an image based on contextual data and historical content presented by the device. The contextual data may indicate a characteristic of the physical environment, the device or the user. The device can determine whether the characteristic indicated by the contextual data matches the historical content presented by the device. If the characteristic indicated by the contextual data matches the historical content presented by the device, the device determines that the user is likely interested in capturing and storing an image of the physical environment. As such, when the characteristic indicated by the contextual data matches the historical content, the device automatically captures and stores an image of the physical environment. By contrast, if the characteristic indicated by the contextual data does not match the historical content presented by the device, the device determines that the user is likely not interested in capturing and storing an image of the physical environment. As such, when the characteristic indicated by the contextual data does not match the historical content, the device does not capture and store an image of the physical environment.

The device can provide the user an option to delete an image that the device automatically captured and stored. For example, after automatically capturing and storing an image, the device can display a notification that includes a delete button. If the user selects the delete button, the device deletes the image that the device automatically captured and stored. The device may delete an automatically stored image if the user does not view the automatically stored image within a certain amount of time. For example, the device can delete an automatically stored image if the user does not view the automatically stored image within seven days.

The device may have the ability to stream video to another device. For example, the device may include a social networking application that allows the device to stream live video for others to view. The social networking application may include a stream button that, when activated, initiates the video streaming. The device may automatically initiate video streaming based on user interest. The device determines whether or not the user may be interested in streaming a video of the physical environment of the device. If the device determines that the user may be interested in streaming a video of the physical environment, the device automatically initiates video streaming. The device may only initiate automatic video streaming when explicit authorization to do so is provided by the user. Automatically initiating video streaming reduces the need for the user to navigate to the social networking application and press the stream button.

The device determines a user interest value that indicates how interested the user is in a physical environment. If the user interest value is greater than a threshold interest value, the device determines that the user is likely interested in storing an image of the physical environment. By contrast, if the user interest value is less than the threshold interest value, the device determines that the user is likely not interested in storing an image of the physical environment. The device may determine the user interest value based on contextual data that indicates a context of the device or a user of the device. The device may determine the threshold interest value based on historical content that the device has captured or presented. The device may store the image in a memory of the device. The device may temporarily store the image in a streaming buffer and subsequently retrieve the image from the streaming buffer to stream the image to another device.

The device can determine the user interest value based on user-specified interest data. For example, the user can indicate that the user is interested in capturing images of a particular subject (e.g., a particular physical article or a particular type of physical environment such as a beach). When the contextual data indicates that the particular subject is in a field-of-view of a camera of the device, the device determines that the user interest value exceeds the threshold interest value, and the device can capture an image of the particular subject. As an example, the user may specify that the user is interested in capturing images of beaches. In this example, when the device detects that the field-of-view of the camera includes a beach, the device can capture and store an image.

FIG. 1A is a diagram that illustrates an example physical environment 10 in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the physical environment 10 includes an electronic device 20, a user 22 of the electronic device 20, a first physical article 30 and a second physical article 32.

In some implementations, the electronic device 20 includes a handheld computing device that can be held by the user 22. For example, in some implementations, the electronic device 20 includes a smartphone, a tablet, a media player, a laptop, or the like. In some implementations, the electronic device 20 includes a wearable computing device that can be worn by the user 22. For example, in some implementations, the electronic device 20 includes a head-mountable device (HMD) or an electronic watch. In various implementations, the electronic device 20 includes an image sensor 24 with a field-of-view 26. The image sensor 24 can capture an image 28 of the physical environment 10. The image 28 includes two-dimensional (2D) representations of the physical articles 30 and 32 because the physical articles 30 and 32 are in the field-of-view 26 of the image sensor 24. The image 28 may include a single image frame. Alternatively, the image 28 may be a part of a sequence of images (e.g., a video). In some implementations, the electronic device 20 can include two or more image sensors 24 that are configured to capture stereoscopic images or video.

In some implementations, the electronic device 20 includes a smartphone or a tablet, and the image sensor 24 includes a rear-facing camera that captures the image 28 when the user 22 points the rear-facing camera towards the physical articles 30 and 32. In some implementations, the electronic device 20 includes an HMD, and the image sensor 24 includes a scene-facing camera that captures the image 28 when the user 22 looks at the physical articles 30 and 32 and causes the scene-facing camera to point in a direction of the physical articles 30 and 32.

In some implementations, the electronic device 20 includes a camera application that generates and presents a graphical user interface (GUI) that allows the user 22 to control operation of the image sensor 24. For example, the GUI includes a capture button that the user 22 can select in order to trigger the image sensor 24 to capture the image 28. The GUI may include a record button that the user 22 can select in order to trigger the image sensor 24 to record a video. In some implementations, the electronic device 20 includes a social networking application that generates and presents a GUI that allows the user 22 to stream a video of the physical environment 10. For example, the GUI of the social networking application may include a button that the user 22 can select to initiate video streaming of the physical environment 10. The video stream may be transmitted to a network element (e.g., a server) that can distribute the video stream to other electronic devices.

In some implementations, the physical articles 30 and 32 include man-made structures such as monuments or buildings. In some implementations, the physical articles 30 and 32 include human-curated objects such as paintings or statues. In some implementations, the physical articles 30 and 32 include natural landmarks such as mountains or waterfalls. In some implementations, the physical articles 30 and 32 include moveable objects such as bicycles or motorcycles.

Figure 1B:
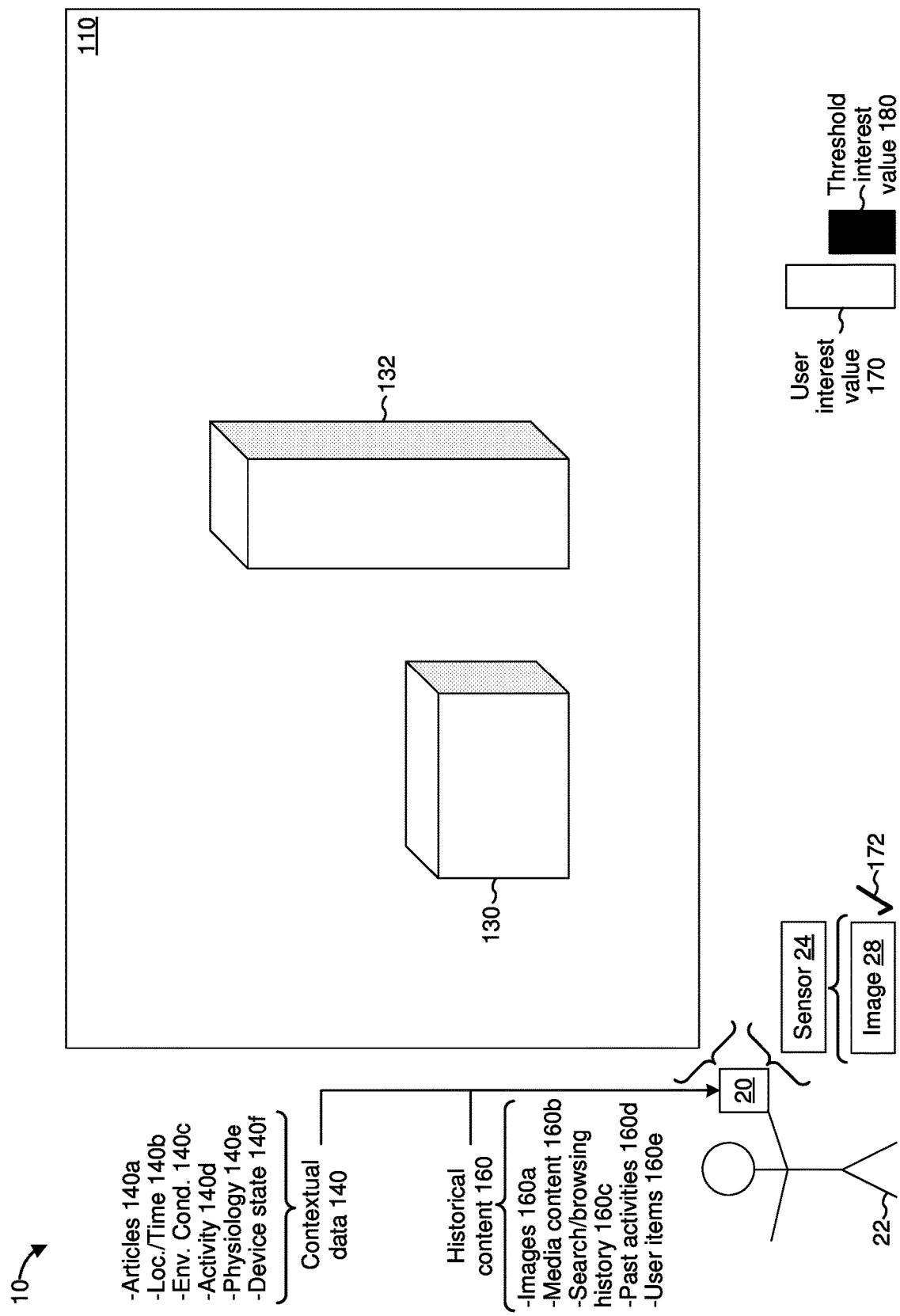

Referring to FIG. 1B, in various implementations, the electronic device 20 presents a graphical environment 110 based on the image 28 captured by the image sensor 24. In some implementations, presenting the graphical environment 110 includes displaying the image 28 on a display of the electronic device 20. As illustrated in FIG. 1B, the graphical environment 110 includes a first graphical object 130 that represents the first physical article 30, and a second graphical object 132 that represents the second physical article 32. In some implementations, the graphical environment 110 is a pass-through representation of the physical environment 10, and the graphical objects 130 and 132 are pass-through representations of the physical articles 30 and 32, respectively. In some implementations, the graphical environment 110 is a video pass-through of the physical environment 10 that the electronic device 20 presents by displaying the image 28. In some implementations, the graphical environment 110 is an optical see-through of the physical environment 10 that the electronic device 20 presents by allowing visible light from the physical environment 10 to enter eyes of the user 22.

In various implementations, the electronic device 20 determines whether or not the user 22 is interested in capturing and storing the image 28 of the physical environment 10. In some implementations, the electronic device 20 obtains contextual data 140 that indicates a context of the physical environment 10, the electronic device 20 or the user 22. The contextual data 140 may indicate a characteristic of the physical environment 10, the electronic device 20 or the user 22. In some implementations, the electronic device 20 obtains an indication of historical content 160 that is associated with the electronic device 20. The historical content 160 may include content items that the electronic device 20 has previously presented and/or content items that the electronic device 20 has previously captured. In various implementations, the electronic device 20 obtains the contextual data 140 and/or the indication of the historical content 160 after obtaining informed consent from the user 22.

In various implementations, the electronic device 20 determines a user interest value 170 based on the contextual data 140 and the historical content 160. The user interest value 170 indicates a level of the interest of the user 22 in the physical environment 10. For example, the user interest value 170 indicates whether the user 22 is likely to capture and store the image 28 of the physical environment 10. The user interest value 170 may indicate whether the user 22 is likely to transmit the image 28 as part of a video stream. In the example of FIG. 1B, the user interest value 170 is greater than a threshold interest value 180. As such, the electronic device 20 determines that the user 22 is likely interested in capturing and storing the image 28. As indicated by a checkmark 172, the electronic device 20 stores the image 28 in response to the user interest value 170 being greater than the threshold interest value 180.

In some implementations, the contextual data 140 includes a list of physical articles 140a that are in the physical environment 10. For example, the contextual data 140 may indicate the presence of the first physical article 30 and the second physical article 32 in the physical environment 10. In some implementations, the electronic device 20 identifies the physical articles 30 and 32 based on an image analysis of the image 28. The historical content 160 may indicate physical articles that the user 22 is interested in capturing an image of. If the list of physical articles 140$a$ includes a physical article that the user 22 may be interested in capturing an image of, the electronic device 20 may set the user interest value 170 to a value that is greater than the threshold interest value 180.

In some implementations, the historical content 160 includes images 160$a$ that the electronic device 20 has previously presented and/or captured. In some implementations, the historical content 160 includes media content items 160$b$ (e.g., movies, TV shows, etc.) that the electronic device 20 has previously presented. In some implementations, the historical content 160 includes a search/browsing history 160$c$ of the electronic device 20. In some implementations, the electronic device 20 identifies a list of physical articles that the user 22 may be interested in capturing an image of based on the images 160$a$, the media content items 160$b$ and/or the search/browsing history 160$c$. For example, if a particular physical article is repeatedly depicted in the images 160$a$ and/or the media content items 160$b$, the electronic device 20 determines that the user 22 is likely interested in capturing an image of that particular physical article. Similarly, if the search/browsing history 160$c$ indicates that the user 22 has recently searched for a particular physical article, the electronic device 20 determines that the user 22 is likely interested in capturing an image of that particular physical article. More generally, in various implementations, the electronic device 20 determines that the user 22 is likely interested in capturing an image of a particular physical article in response to that particular physical article being represented more than a threshold number of times in the images 160$a$, the media content items 160$b$ or the search/browsing history 160$c$ associated with a threshold time period occurring prior to a current time.

In some implementations, the contextual data 140 indicates a geographical location 140$b$ of the electronic device 20 and/or a time of day. For example, the contextual data 140 may indicate that the electronic device 20 is currently at a beach during sunset. The historical content 160 may indicate locations that the user 22 may be interested in capturing an image of. If the geographical location 140$b$ of the electronic device 20 matches a location that the user 22 may be interested in capturing an image of, the electronic device 20 sets the user interest value 170 to a value that is greater than the threshold interest value 180. In some implementations, the electronic device 20 identifies locations that the user 22 may be interested in capturing images of based on locations depicted in the images 160$a$, the media content items 160$b$ or the search/browsing history 160$c$. For example, if the user 22 has recently watched several videos about a national park and the user 22 performs a search for hotels near the national park, the electronic device 20 determines that the user 22 is likely interested in capturing images of the national park. In this example, when the geographical location 140$b$ indicates that the electronic device 20 is at the national park, the electronic device 20 can automatically capture and store images without requiring the user 22 to provide a user input to capture and store images.

In some implementations, the contextual data 140 indicates environmental conditions 140$c$ of the physical environment 10. In some implementations, the environmental conditions 140$c$ may indicate an amount of ambient light, an ambient temperature, an ambient sound level, and/or whether it is sunny, rainy, cloudy, snowy, etc. The historical content 160 may indicate environmental conditions during which the user 22 may be interested in capturing an image of the physical environment 10. If the environmental conditions 140$c$ match the environmental conditions during which the user 22 may be interested in taking pictures, the electronic device 20 sets the user interest value 170 to a value that is greater than the threshold interest value 180. In some implementations, the electronic device 20 identifies environmental conditions during which the user 22 may be interested in capturing images based on environmental conditions depicted in the images 160$a$, the media content items 160$b$ or the search/browsing history 160$c$. For example, if the user 22 recently viewed pictures of snow falls, the electronic device 20 determines that the user 22 is likely interested in capturing images when the environmental conditions 140$c$ indicate that it is snowing in the physical environment 10. In this example, when the environmental conditions 140$c$ indicate that it is snowing in the physical environment 10, the electronic device 20 can automatically capture and store images without requiring the user 22 to provide a user input to capture and store images.

In some implementations, the contextual data 140 indicates a user activity 140$d$ that the user 22 is currently performing. The historical content 160 may indicate past activities 160$d$ of the user 22 (e.g., activities that the user 22 performed previously). Alternatively or additionally, the past activities 160$d$ may include activities depicted in the images 160$a$ and/or the media content items 160$b$, and/or activities that match the search/browsing history 160$c$. If the user activity 140$d$ matches the past activities 160$d$, the electronic device 20 sets the user interest value 170 to a value that is greater than the threshold interest value 180. For example, if the past activities 160$d$ include snowboarding and the user activity 140$d$ indicates that the user 22 is currently snowboarding, the electronic device 20 determines that the user 22 is likely interested in capturing images while the user 22 is snowboarding. In this example, while the user 22 is snowboarding, the electronic device 20 can automatically capture and store images without requiring the user 22 to provide a user input to capture and store images.

In some implementations, the electronic device 20 determines the user activity 140$d$ based on the contextual data 140. In some implementations, the electronic device 20 determines the user activity 140$d$ based on environmental data captured by one or more environmental sensors of the electronic device 20. For example, in some implementations, the electronic device 20 determines the user activity 140$d$ based on audible signal data captured by an audio sensor (e.g., based on background audio). As an example, the electronic device 20 may determine that the user 22 is near a beach when the audible signal data includes sounds of ocean waves crashing on a shore. In some implementations, the electronic device 20 determines the user activity 140$d$ based on data from an inertial measurement unit (IMU) that indicates a movement of the user 22. As an example, the electronic device 20 may determine that the user 22 is jogging in response to the IMU data matching a jogging pattern. In some implementations, the electronic device 20 determines the user activity 140$d$ based on image data captured by the image sensor 24. For example, the image sensor 24 may periodically capture images that the electronic device 20 analyzes to identify the user activity 140$d$.

In some implementations, the contextual data 140 indicates a physiological measurement 140$e$ related to the user 22. In some implementations, the physiological measurement 140e includes a heart rate value captured by a heart rate sensor, a blood pressure value captured by a blood pressure sensor, a perspiration value captured by a perspiration sensor, a blood glucose value captured by a blood glucose sensor, a voice input (e.g., an utterance) captured by a microphone, a facial image (e.g., a facial expression) captured by a user-facing image sensor, or any other physiological measurement related to the user. In some implementations, the electronic device 20 determines the user interest value 170 based on the physiological measurement 140e. In some implementations, the electronic device 20 sets the user interest value 170 to a value that is greater than the threshold interest value 180 in response to the physiological measurement 140e being greater than a threshold physiological value that corresponds with a relatively high degree of excitement. For example, the electronic device 20 may determine that the user 22 is interested in storing the image 28 when the heart rate of the user is greater than a threshold heart rate, when the blood pressure of the user is greater than a threshold blood pressure value, when the user 22 is perspiring more than a threshold perspiration level, when the user 22 is vocalizing his/her excitement (e.g., by saying "WOW!"), and/or when the user 22 has a particular facial expression (e.g., when the user is smiling). In some implementations, the electronic device 20 determines that the user 22 is likely interested in storing the image 28 when the physiological measurement 140e matches a historical physiological measurement when at least a subset of the images 160a were previously stored.

In some implementations, the contextual data 140 indicates a device state 140f. In some implementations, the device state 140f indicates a power level of the electronic device 20, an amount of memory available to the electronic device 20, and/or a network connectivity of the electronic device 20. In some implementations, the electronic device 20 automatically captures and stores the image 28 when the user interest value 170 is greater than the threshold interest value 180 and the device state 140f indicates a power level that is greater than a threshold power level. In some implementations, the electronic device 20 does not automatically capture and store the image 28 when the user interest value 170 is greater than the threshold interest value 180 and the device state 140f indicates a power level that is less than the threshold power level.

In some implementations, the electronic device 20 automatically stores the image 28 when the user interest value 170 is greater than the threshold interest value 180 and the device state 140f indicates that the amount of memory available to the electronic device 20 is greater than a threshold amount of memory. In some implementations, the electronic device 20 does not automatically store the image 28 when the user interest value 170 is greater than the threshold interest value 180 and the device state 140f indicates that the amount of memory available to the electronic device 20 is less than the threshold amount of memory.

In some implementations, the electronic device 20 automatically stores the image 28 in a streaming buffer where the image 28 is queued for streaming when the user interest value 170 is greater than the threshold interest value 180 and the network connectivity of the electronic device 20 is greater than a threshold connectivity level (e.g., when the electronic device 20 has access to Wi-Fi). In some implementations, the electronic device 20 does not automatically store the image 28 in the streaming buffer when the user interest value 170 is greater than the threshold interest value 180 and the network connectivity of the electronic device 20 is less than the threshold connectivity level (e.g., when the electronic device 20 does not have access to Wi-Fi).

In some implementations, the electronic device 20 determines that the user 22 is likely interested in storing the image 28 when the device state 140f matches a historical device state when at least a subset of the images 160a were previously captured and stored.

In some implementations, the historical content 160 includes user-curated content items 160e. The user-curated content items 160e may include notes stored in association with a notes application and/or a list stored in association with a task management application. In some implementations, the user-curated content items 160e may include a list of places to visit. In such implementations, when the geographical location 140b matches one of the places on the list, the electronic device 20 determines that the user 22 is likely interested in capturing and storing the image 28. In some implementations, the user-curated content items 160e may include a list of physical articles (e.g., a list of items to purchase). In such implementations, when one of the physical articles on the list is in the field-of-view 26 of the electronic device 20, the electronic device 20 determines that the user 22 is likely interested in capturing and storing the image 28. More generally, when the contextual data 140 indicates that the physical environment 10 includes a physical article that matches a physical article depicted (e.g., mentioned or described) in the user-curated content items 160e, the electronic device 20 sets the user interest value 170 to a value that is greater than the threshold interest value 180.

In some implementations, the electronic device 20 stores the image 28 in association with a photos application. In some implementations, the electronic device 20 stores the image 28 in a separate album that includes automatically-stored images and videos. In some implementations, the electronic device 20 stores the image 28 in a streaming buffer where the image 28 is queued for video streaming. In some implementations, the electronic device 20 stores the image 28 for a threshold time period and if the image 28 is not viewed during that threshold time period, then the electronic device 20 automatically deletes the image 28.

In some implementations, the user interest value 170 indicates which of the physical articles 30 and 32 the user 22 is interested in. For example, the user interest value 170 may indicate that the user 22 is more interested in the first physical article 30 than the second physical article 32. In such implementations, the electronic device 20 can adjust a configuration of the image sensor 24 so that the image sensor 24 is focused on the first physical article 30. For example, the electronic device 20 can adjust a zoom level of the image sensor 24 so that the image sensor 24 zooms-in on the first physical article 30 and the image 28 depicts the first physical article 30 and not the second physical article 32. As another example, the electronic device 20 can pan the image sensor 24 so that the image 28 depicts more of the first physical article 30 and less of the second physical article 32.

Figure 1C:
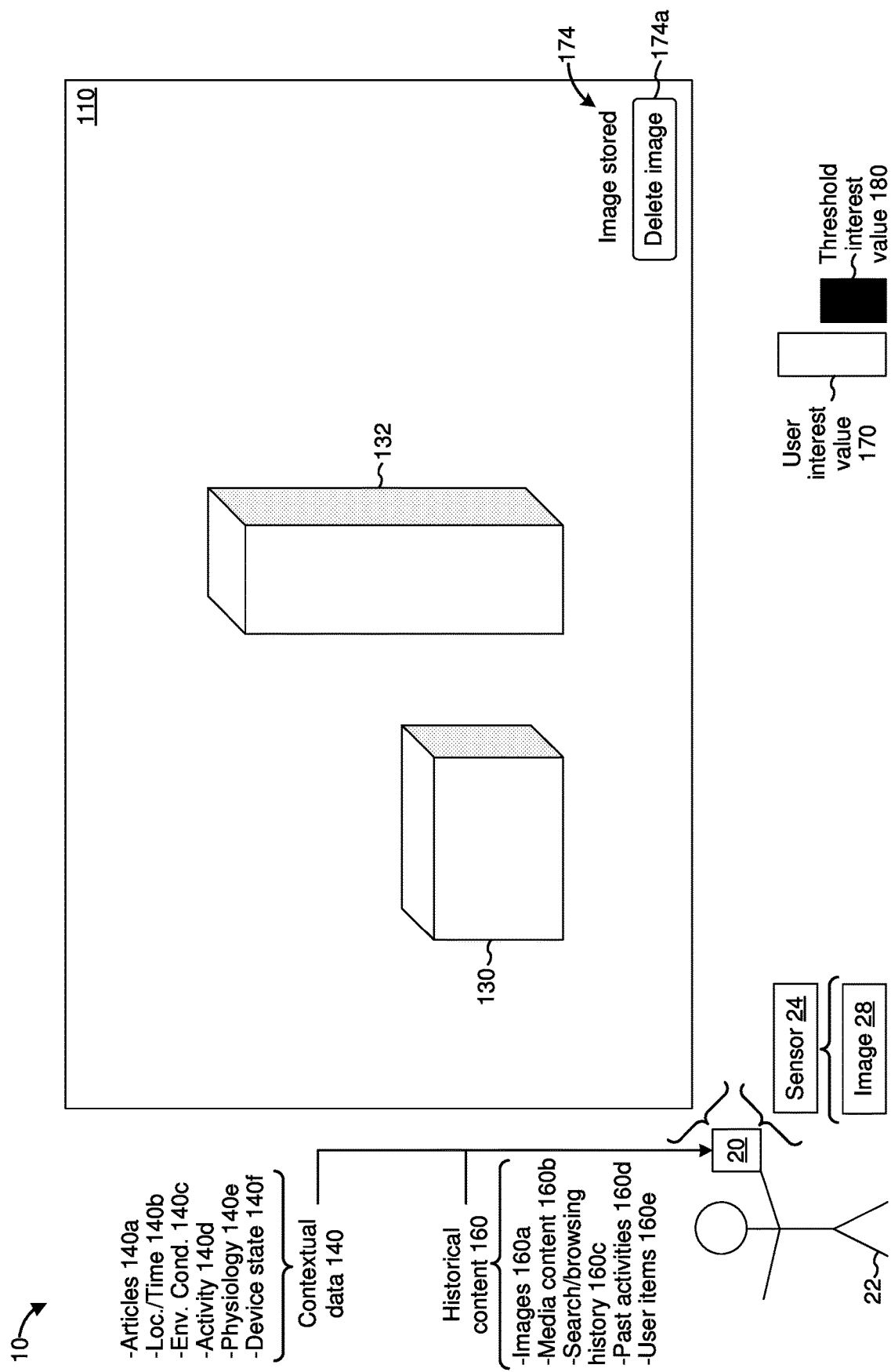

Referring to FIG. 1C, in some implementations, the electronic device 20 displays an image stored notification 174 that indicates that the electronic device 20 has stored the image 28. In some implementations, the image stored notification 174 includes a delete affordance 174a for deleting the image 28 from memory. In some implementations, the delete affordance 174a includes a button that, when activated by the user 22, causes the electronic device 20 to delete the image 28 from the memory.

Figure 1D:
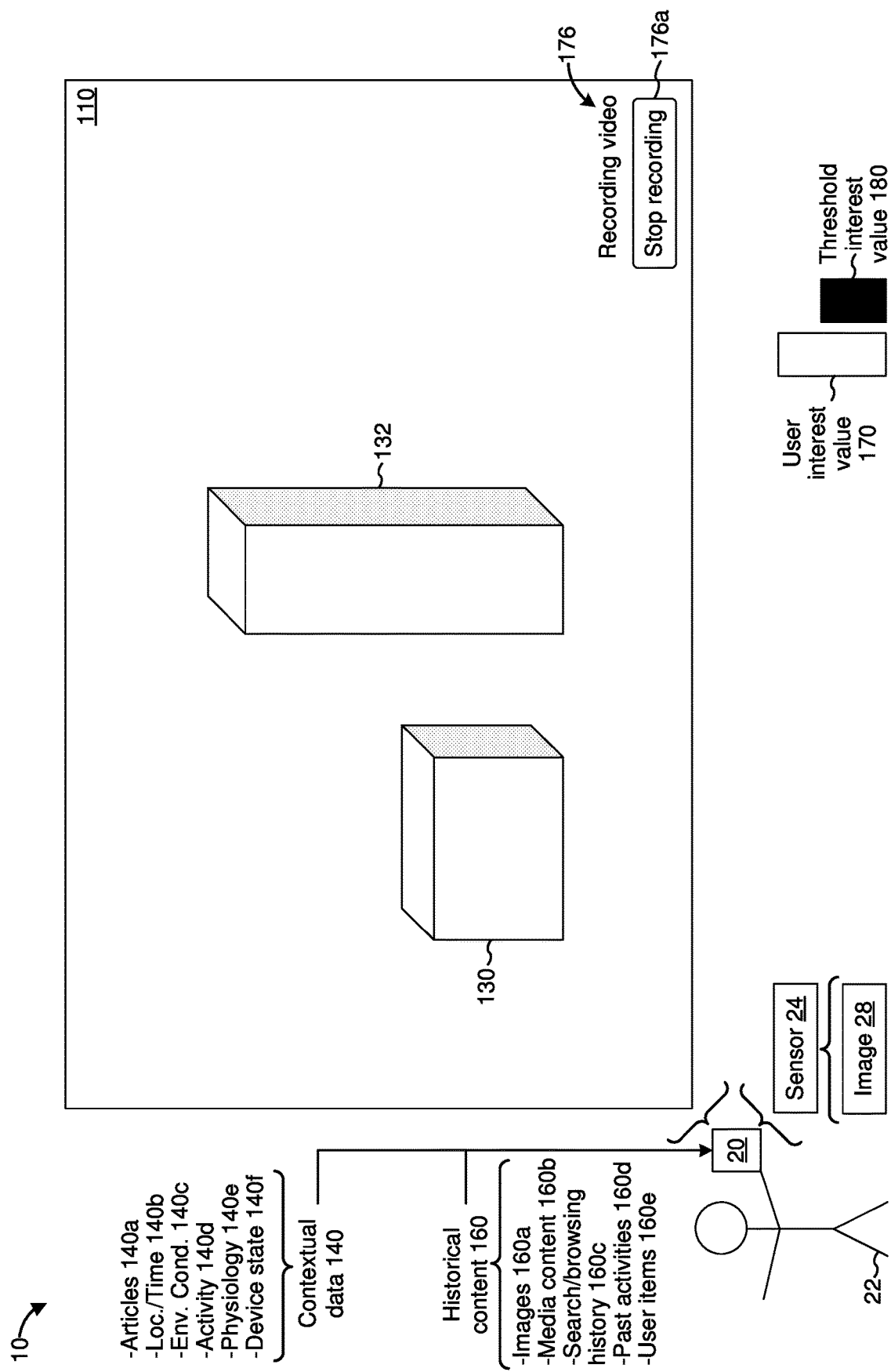

Referring to FIG. 1D, in some implementations, automatically capturing and storing the image 28 includes automatically initiating a video recording of the physical environment 10. Automatically initiating the video recording includes automatically starting video recording without requiring the user to navigate to a GUI of the camera application and pressing a record button. When the electronic device 20 automatically starts recording video, the electronic device 20 displays a recording video notification 176 indicating that the electronic device 20 has automatically started recording video. The recording video notification 176 includes a stop affordance 176a for stopping the video recording that the electronic device 20 initiated automatically. The electronic device 20 stops recording video when the user selects the stop affordance 176a. In some implementations, in response to detecting a selection of the stop affordance 176a, the electronic device 20 deletes a video that the electronic device 20 automatically recorded prior to the user 22 selecting the stop affordance 176a.

Figure 1E:
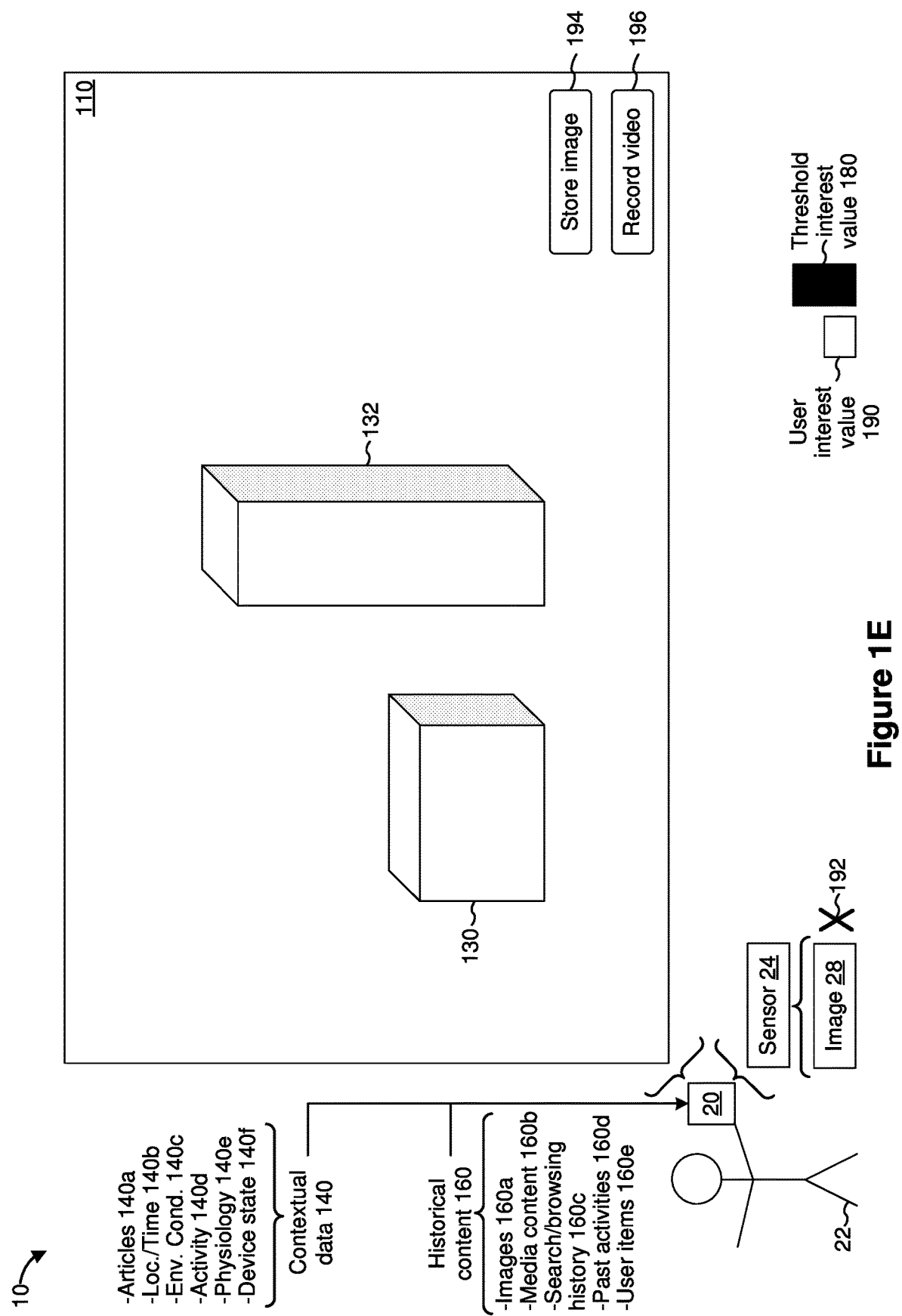

Referring to FIG. 1E, in some implementations, the electronic device 20 determines a user interest value 190 that is less than the threshold interest value 180. When the user interest value 190 is less than the threshold interest value 180, the electronic device 20 does not automatically capture or store the image 28 as indicated by a cross 192. As such, the image 28 is discarded (e.g., purged). In some implementations, when the user interest value 190 is less than the threshold interest value 180, the electronic device 20 displays a store image affordance 194 that provides the user 22 an option to capture and store an image (e.g., an option to store the image 28). In some implementations, when the user interest value 190 is less than the threshold interest value, the electronic device 20 displays a record video affordance 196 that provides the user 22 an option to record a video.

Figure 2:
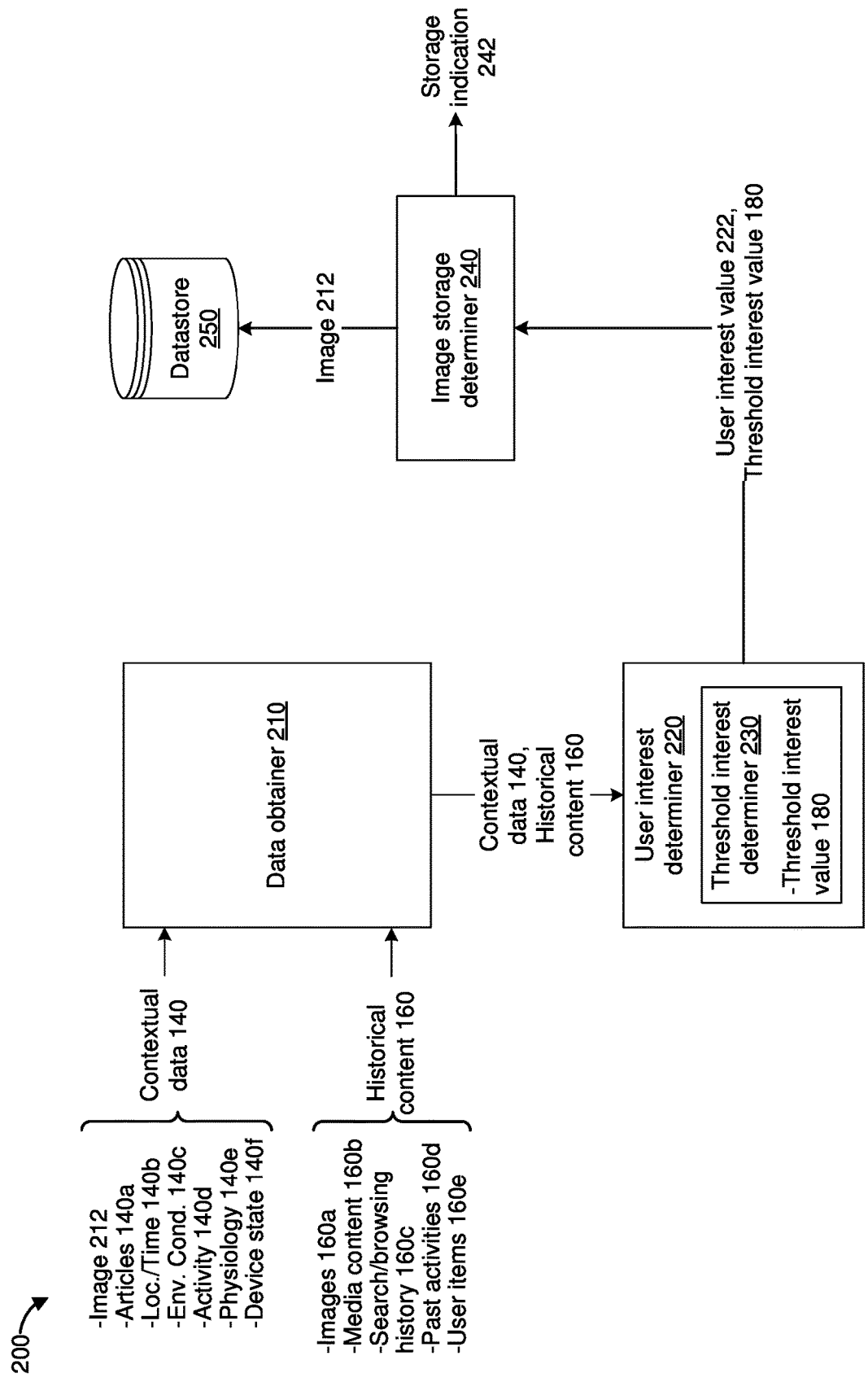
FIG. 2 is a block diagram of a system that captures and stores an image of a physical environment in accordance with some implementations.

FIG. 2 is a block diagram of a system 200 that automatically captures and stores an image of a physical environment based on user interest. In some implementations, the system 200 includes a data obtainer 210, a user interest determiner 220, a threshold interest determiner 230, an image storage determiner 240 and a datastore 250. In various implementations, the system 200 resides at (e.g., is implemented by) the electronic device 20 shown in FIGS. 1A-1E.

In various implementations, the data obtainer 210 obtains the contextual data 140 and the indication of the historical content 160. In some implementations, the data obtainer 210 receives the contextual data 140 from a set of one or more sensors of the electronic device 20 shown in FIGS. 1A-1E. In some implementations, the contextual data 140 includes an image 212 (e.g., the image 28 shown in FIGS. 1A-1E) that the data obtainer 210 receives from an image sensor (e.g., the image sensor 24 shown in FIGS. 1A-1E). In some implementations, the image 212 is an image of a physical environment (e.g., the physical environment 10 shown in FIGS. 1A-1E). In some implementations, the image 212 is an image of the user 22 shown in FIGS. 1A-1E. For example, the image 212 may be a facial image that includes a representation of a face of the user 22.

In various implementations, the data obtainer 210 determines the list of physical articles 140a that are in the physical environment based on the image 212. In some implementations, the data obtainer 210 receives the geographical location 140b from a location sensor. In some implementations, the data obtainer 210 receives an indication of the environmental conditions 140c from an environmental sensor (e.g., a temperature sensor, a humidity sensor, etc.). In some implementations, the data obtainer 210 determines the environmental conditions 140c based on the image 212. In some implementations, the data obtainer 210 determines the user activity 140d based on sensor data that the data obtainer 210 receives from a set of one or more sensors (e.g., sensor data from an inertial measurement unit (IMU) sensor) and/or based on the image 212. In some implementations, the data obtainer 210 receives the physiological measurement 140e from a set of one or more physiological sensors (e.g., a heart rate monitor, a perspiration monitor, a blood glucose monitor, blood pressure sensor, etc.). In some implementations, the data obtainer determines the device state 140f based on data from a device controller (e.g., based on battery status data from a battery controller, based on memory availability data from a memory controller and/or based on network connectivity data from a network controller).

In various implementations, the data obtainer 210 determines the historical content 160 by monitoring device usage. For example, in some implementations, the data obtainer 210 identifies the images 160a and the media content items 160b that the electronic device 20 previously presented and/or captured by tracking images and media content items that the electronic device 20 has presented and/or captured in the past. In some implementations, the data obtainer 210 retrieves the indication of the historical content 160 from a log that stores the indication of the historical content 160. In some implementations, the data obtainer 210 retrieves the user-curated content items 160e from applications that are installed on the electronic device 20 (e.g., from data stored in association with the notes application and/or the task management application).

In various implementations, the user interest determiner 220 determines a user interest value 222 (e.g., the user interest value 170 shown in FIGS. 1B-1D and/or the user interest value 190 shown in FIG. 1E) based on the contextual data 140 and the historical content 160. As described in relation to FIG. 1B, in various implementations, the user interest determiner 220 sets the user interest value 222 based on a match between the contextual data 140 and the historical content 160. In some implementations, the user interest value 222 indicates a degree of similarity between the contextual data 140 and the historical content 160. For example, if the image 212 is within a similarity threshold of the images 160a, the user interest determiner 220 sets the user interest value 222 to a relatively high value (e.g., to a value that may be greater than the threshold interest value 180). By contrast, if the image 212 is not within the similarity threshold of the images 160a, the user interest determiner 220 sets the user interest value 222 to a relatively low value (e.g., to a value that may be less than the threshold interest value 180).

In some implementations, when the list of physical articles 140a specifies a physical article that has been repeatedly depicted in the images 160a and/or in the media content items 160b, the user interest determiner 220 may set the user interest value 222 to a value that is greater than the threshold interest value 180. In some implementations, when the search/browsing history 160e indicates that the list of physical articles 140a specifies a physical article that has been presented in response to recent searches, the user interest determiner 220 may set the user interest value 222 to a value that is greater than the threshold interest value 180. In some implementations, when the geographical location 140b and/or the environmental conditions 140c match a geographical condition and/or environmental conditions, respectively, repeatedly depicted in the images 160a, the media content items 160b or the search/browsing history 160c, the user interest determiner 220 may set the user interest value 222 to a value that is greater than the threshold interest value 180.

In some implementations, when the user activity 140d matches one of the past activities 160d, the user interest determiner 220 may set the user interest value 222 to a value that is greater than the threshold interest value 180. In some implementations, when the physiological measurement 140e matches historical physiological measurements when the user 22 manually captured pictures, the user interest determiner 220 may set the user interest value 222 to a value that is greater than the threshold interest value 180. In some implementations, when the device state 140f matches historical device states when the user 22 manually captured pictures, the user interest determiner 220 may set the user interest value 222 to a value that is greater than the threshold interest value 180.

In some implementations, the threshold interest determiner 230 determines the threshold interest value 180 based on the historical content 160. In some implementations, the threshold interest value 180 indicates types of physical environments that interest the user 22. For example, the threshold interest value 180 may indicate whether the user 22 is more interested in physical environments with natural landmarks (e.g., mountains, rivers, beaches, etc.) or man-made structures (e.g., skyscrapers, museums, etc.). In some examples, the threshold interest value 180 indicates that the user 22 is more interested in natural landmarks than man-made structures in response to the images 160a, the media content items 160b and the search/browsing history 160c being more closely related to natural landmarks than man-made structures.

In some implementations, the threshold interest value 180 indicates physical articles that interest the user 22. For example, the threshold interest value 180 may indicate whether the user 22 is interested in taking pictures of motorcycles. In some examples, the threshold interest determiner 230 identifies the physical articles that the user 22 is interested in based on the images 160a and the media content items 160b that the user 22 has previously captured or viewed. In some implementations, the threshold interest determiner 230 identifies the physical articles that the user 22 is interested in based on the search/browsing history 160c. In some implementations, the threshold interest value 180 indicates environmental conditions that interest the user 22. For example, the threshold interest value 180 may indicate whether the user 22 is interested in taking pictures on sunny days, snowy days, cloudy days, rainy days, etc. In some implementations, the threshold interest determiner 230 identifies the environmental conditions that the user is interested in based on environmental conditions depicted in the images 160a and the media content items 160b.

In some implementations, the threshold interest value 180 indicates activities that interest the user 22. In some implementations, the threshold interest determiner 230 identifies the activities that interest the user 22 based on the past activities 160d. In various implementations, the threshold interest determiner 230 determines the threshold interest value 180 based on the user-curated content items 160e. For example, in some implementations, the user-curated content items 160e indicate a list of places that the user 22 wants to visit. In this example, the threshold interest determiner 230 determines the threshold interest value 180 based on the list of places that the user 22 wants to visit. As another example, in some implementations, the user-curated content items 160e indicate a list of physical articles that the user 22 may be interested in purchasing. In this example, the threshold interest determiner 230 determines the threshold interest value 180 based on the list of physical articles that the user may be interested in purchasing.

In various implementations, the image storage determiner 240 determines whether or not to automatically store the image 212 in the datastore 250 based on the user interest value 222 and the threshold interest value 180. In some implementations, the image storage determiner 240 determines to automatically store the image 212 in the datastore 250 in response to the user interest value 222 being greater than the threshold interest value 180. In such implementations, the image storage determiner 240 stores the image 212 in the datastore 250 without detecting a user input that corresponds to a request to store the image 212 in the datastore 250. By contrast, in some implementations, the image storage determiner 240 determines not to store the image 212 in the datastore 250 in response to the user interest value 222 being less than the threshold interest value 180. In some implementations, the image storage determiner 240 generates and presents a storage indication 242 in response to automatically storing the image 212 in the datastore 250. For example, the image storage determiner 240 generates and presents the image stored notification 174 shown in FIG. 1C.

In some implementations, the image storage determiner 240 stores the image 212 in the datastore 250 for a threshold amount of time. If the image 212 is not viewed within the threshold amount of time, the image storage determiner 240 can delete the image 212 from the datastore 250. In some implementations, the image storage determiner 240 provides an option to delete the image 212 after the image 212 is automatically stored in the datastore 250. For example, the image storage determiner 240 displays the delete affordance 174a shown in FIG. 1C. In some implementations, the datastore 250 resides at the electronic device 20. Alternatively, in some implementations, the datastore 250 resides at another device (e.g., at a server or a cloud computing platform). In some implementations, the datastore 250 represents a queue that includes images that are to be streamed and storing the image 212 in the queue results in the image 212 being transmitted as a part of a video stream.

In various implementations, the system 200 includes a machine learned model that is trained to determine whether or not to capture and/or store an image or a video based on an input vector. In some implementations, the input vector includes at least some of the contextual data 140 and/or the historical content 160. In some implementations, the machine learned model implements a combination of the user interest determiner 220, the threshold interest determiner 230 and the image storage determiner 240. In some implementations, the machine learned model includes a neural network system (e.g., a set of one or more neural networks).

Figure 3:
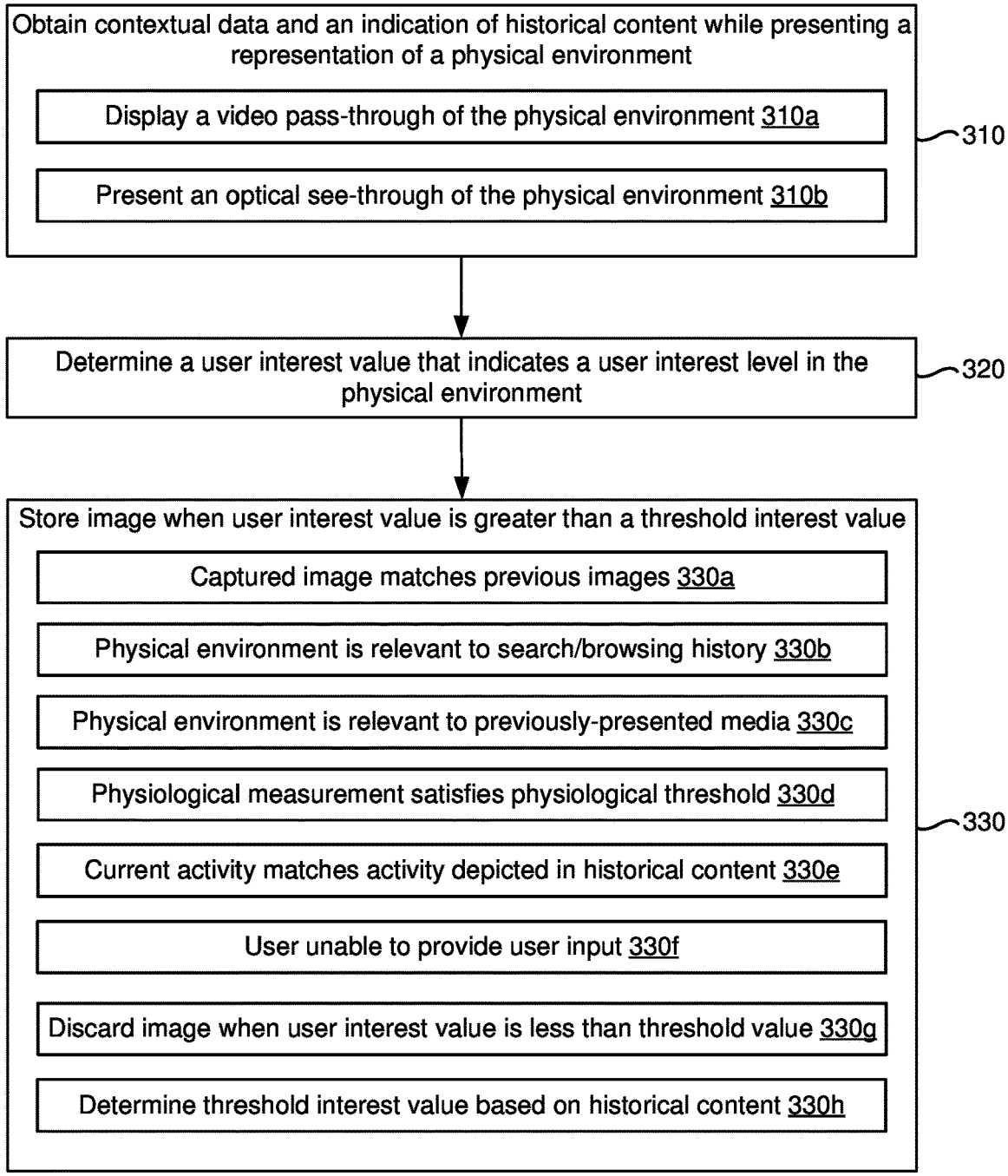
FIG. 3 is a flowchart representation of a method of capturing and storing an image of a physical environment in accordance with some implementations.

FIG. 3 is a flowchart representation of a method 300 for automatically capturing and storing an image based on user interest. In various implementations, the method 300 is performed by a device including a display, an image sensor, a non-transitory memory and one or more processors coupled with the display, the image sensor and the non-transitory memory (e.g., the electronic device 20 shown in FIGS. 1A-1E and/or the system 200 shown in FIG. 2). In some implementations, the method 300 is performed by processing logic, including hardware, firmware, software, or a combination thereof. In some implementations, the method 300 is performed by a processor executing code stored in a non-transitory computer-readable medium (e.g., a memory).

As represented by block 310, in various implementations, the method 300 includes, while presenting a representation of a physical environment of the device, obtaining contextual data that indicates a characteristic of the physical environment, the device or a user of the device and obtaining an indication of historical content associated with the device. In some implementations, presenting the representation of the physical environment includes presenting a pass-through representation of the physical environment. As represented by block 310*a*, in some implementations, presenting the pass-through representation of the physical environment includes displaying a video pass-through of the physical environment. For example, the method 300 includes capturing an image of the physical environment via the image sensor and displaying the captured image on a video pass-through display (e.g., an opaque display) of the device. As represented by block 310*b*, in some implementations, presenting a pass-through representation of the physical environment includes presenting an optical see-through of the physical environment via an optical see-through display. For example, the method 300 includes allowing visible light from the physical environment to enter eyes of the user through the optical see-through display.

In some implementations, obtaining the contextual data includes receiving an image captured by the image sensor. For example, receiving the image 28 shown in FIGS. 1A-1E and/or the image 212 shown in FIG. 2. In some implementations, the method 300 includes receiving a first image of the physical environment and receiving a second image of the user (e.g., a second image showing a body pose and/or a facial expression of the user). In some implementations, obtaining the contextual data includes determining a list of physical articles that are in the physical environment (e.g., the list of physical articles 140*a* shown in FIGS. 1B-2). In some implementations, obtaining the contextual data includes determining a geographical location of the device (e.g., the geographical location 140*b* shown in FIGS. 1B-2) and/or determining a time of day. In some implementations, obtaining the contextual data includes determining environmental conditions (e.g., the environmental conditions 140*c* shown in FIGS. 1B-2) of the physical environment based on sensor data captured by environmental sensors such as a thermometer and/or based on the image of the physical environment. In some implementations, obtaining the contextual data includes identifying an activity of the user (e.g., the user activity 140*d* shown in FIGS. 1B-2) based on sensor measurements and/or based on an image of the user. In some implementations, obtaining the contextual data includes receiving a physiological measurement (e.g., the physiological measurement 140*e* shown in FIGS. 1B-2) of the user from a physiological sensor such as a heart rate monitor, a blood glucose monitor, etc. In some implementations, obtaining the contextual data includes receiving information regarding a device state (e.g., the device state 140*f* shown in FIGS. 1B-2) such as a battery level, a memory state and/or a network connectivity state.

In some implementations, obtaining the indication of the historical content includes receiving an indication of historical content that the electronic device has presented in the past. In some implementations, obtaining the indication of the historical content includes receiving an indication of media captured by the electronic device in the past. For example, the method 300 includes obtaining images that the device has captured and/or presented in the past (e.g., the images 160*a* shown in FIGS. 1B-2). In some implementations, the method 300 includes obtaining media content items that the device has captured and/or presented in the past (e.g., the media content items 160*b* shown in FIGS. 1B-2). In some implementations, the method 300 includes obtaining a search history and/or a browsing history of the device (e.g., the search/browsing history 160*c* shown in FIGS. 1B-2). In some implementations, the method 300 includes obtaining indications of past activities (e.g., the past activities 160*d* shown in FIGS. 1B-2) that the user has performed or has expressed an interest in performing (e.g., by viewing images or videos of such activities being performed). In some implementations, the method 300 includes obtaining user-curated content items that indicate the user's interest (e.g., the user-curated content items 160*e* shown in FIGS. 1B-2).

As represented by block 320, in some implementations, the method 300 includes determining, based on the characteristic indicated by the contextual data and the historical content, a user interest value that indicates a user interest level in the physical environment. In some implementations, the method 300 includes determining a user interest level in a particular object that is located in the physical environment. For example, as shown in FIG. 1B, the electronic device 20 determines the user interest value 170 that indicates a user interest level in the physical environment or in at least one of the physical articles 30 and 32 shown in FIG. 1A. In some implementations, the method 300 includes determining the user interest value by comparing the contextual data with the historical content. In some implementations, the user interest value is a function of a similarity between the contextual data and the historical content. For example, the user interest value is proportional to the similarity between the contextual data and the historical content. As an example, the more similar the contextual data and the historical content are, the greater the user interest value may be.

As represented by block 330, in various implementations, the method 300 includes storing an image captured by the image sensor in response to the user interest value being greater than a threshold interest value. For example, as indicated by the checkmark 172 in FIG. 1B, the electronic device 20 stores the image 28 in response to the user interest value 170 being greater than the threshold interest value 180. In some implementations, the method 300 includes displaying an indication that the image has been automatically stored without requiring a user input that corresponds to a request to capture and/or store the image. For example, the method 300 includes storing the image of the physical environment without requiring the user to navigate to a camera GUI and press an image capture button or a video record button in the camera GUI.

As represented by block 330*a*, in some implementations, the contextual data includes the image captured by the image sensor and the historical content includes previous images captured by the image sensor or presented by the device. In such implementations, determining the user interest value includes determining a similarity score that indicates a degree of similarity between the image captured by the image sensor and the previous images. In such implementations, the user interest value is determined to have a value that is greater than the threshold interest value in response to the similarity score being greater than a threshold similarity score. In some implementations, the image captured by the image sensor includes a two-dimensional representation of a physical article in the physical environment, and the similarity score indicates a degree of similarity between the physical article in the physical environment and an object depicted in at least one of the previous images. As an example, when objects in the physical environment resemble objects depicted in the previous images, the device determines that the user is likely interested in capturing an image of the physical environment. As another example, when an activity being performed in the physical environment resembles activities that are depicted in previous images, the device determines that the user is likely interested in capturing an image of the physical environment. For example, referring to FIG. 2, when the image 212 is within a similarity threshold of at least a subset of the images 160a, the user interest determiner 220 sets the user interest value 222 to a value that is greater than the threshold interest value 180.

As represented by block 330b, in some implementations, the historical content includes a browsing history or a search history of the device. In some implementations, determining the user interest value includes determining a relevance score that indicates a relevance of the physical environment to the browsing history or the search history of the device. In some implementations, the user interest value is determined to have a value that is greater than the threshold interest value in response to the relevance score being greater than a threshold relevance score. In some implementations, the relevance score indicates whether or not a physical article in the physical environment is within a similarity threshold of an object related to the browsing history or the search history. For example, the relevance score indicates a similarity of the physical article to an object presented in response to search queries or pages browsed. As an example, if the user recently read about a particular monument and that monument is in a field-of-view of the device, the device determines that the user is likely interested in capturing and storing a picture of the monument. Referring to FIG. 2, the user interest determiner 220 determines the user interest value 222 based on how well the contextual data 140 matches the search/browsing history 160c.

As represented by block 330c, in some implementations, the historical content includes media content items (e.g., images and/or videos) that the device has presented within a recency threshold (e.g., within a particular period of time, for example, within the last 2 days, 6 months, etc.). In some implementations, determining the user interest value includes determining a relevance score that indicates a relevance of the physical environment to the media content items. In some implementations, the user interest value is determined to have a value that is greater than the threshold interest value in response to the relevance score being greater than a threshold relevance score. In some implementations, the relevance score indicates whether the physical environment matches an environment depicted in at least one of the media content items. For example, when recently-viewed media content items include scenes from Mount Rushmore, and the physical environment of the device is Mount Rushmore, the relevance score may indicate that the physical environment is highly relevant and that the user may be interested in capturing an image of the physical environment. Referring to FIG. 2, the user interest determiner 220 determines the user interest value 222 based on a match between the image 212 and the images 160a or the media content items 160b.

As represented by block 330d, in some implementations, the characteristic indicated by the contextual data includes a physiological measurement (e.g., a heart rate, a gaze vector, a perspiration level, a voice input characteristic, etc.). In some implementations, determining the user interest value includes determining whether the physiological measurement satisfies a physiological threshold. For example, the method 300 includes determining whether or not a heart rate is above a threshold heart rate, determining whether a gaze of the user is fixated at a particular object for more than a threshold time, determining whether a perspiration level of the user is greater than a perspiration threshold, and/or determining whether a frequency or an amplitude of an utterance is greater than a threshold frequency or a threshold amplitude, respectively, that indicates excitement. In some implementations, the user interest value is determined to have a value that is greater than the threshold interest value in response to the physiological measurement satisfying the physiological threshold. For example, storing the image when the heart rate is above the threshold heart rate, when the gaze of the user is fixated at a particular object for more than the threshold time, when the perspiration level of the user is greater than the perspiration threshold, and/or when the frequency or the amplitude of the utterance is greater than the threshold frequency or the threshold amplitude, respectively, that indicates excitement.

In some implementations, the physiological measurement includes a heart rate value and the physiological threshold includes a threshold heart rate value. In some implementations, the method 300 includes obtaining the heart rate value from a heart rate sensor. In some implementations, the user interest value is determined to have a value that is greater than the threshold interest value in response to the heart rate value being greater than the threshold heart rate value.

In some implementations, the physiological measurement includes a perspiration rate value and the physiological threshold includes a threshold perspiration rate value. In some implementations, the method 300 includes obtaining the perspiration rate value from a perspiration rate sensor. In some implementations, the user interest value is determined to have a value that is greater than the threshold interest value in response to the perspiration rate value being greater than the threshold perspiration rate value.

In some implementations, the physiological measurement includes a gaze vector that indicates a gaze position, a gaze intensity or a gaze duration of a user of the device, and the physiological threshold includes a threshold time duration. In some implementations, the user interest value is determined to have a value that is greater than the threshold interest value in response to the gaze position corresponding to a particular physical article in the physical environment for the threshold time duration. For example, when the user looks at a particular object for a certain amount of time, the device determines that the user is likely interested in capturing an image of that particular object and the device automatically captures and stores an image of that particular object.

In some implementations, the physiological measurement includes a facial expression of a user of the device and the physiological threshold includes a threshold facial expression (e.g., an expression that conveys surprise or an expression that conveys happiness). In some implementations, the user interest value is determined to have a value that is greater than the threshold interest value in response to the facial expression matching the threshold facial expression. For example, the device may automatically capture and store an image of the physical environment when the user has a smiling expression, a surprised expression or an amazed expression.

In some implementations, the physiological measurement includes a voice characteristic associated with an utterance of a user of the device and the physiological threshold includes a threshold voice characteristic. In some implementations, the user interest value is determined to have a value that is greater than the threshold interest value in response to the voice characteristic satisfying the threshold voice characteristic. As an example, when the voice characteristic indicates that an amplitude of the utterance is greater than a threshold amplitude, and/or when the voice characteristic indicates that a frequency of the utterance is greater than a threshold frequency, the electronic device automatically captures and stores an image of the physical environment.

As represented by block 330e, in some implementations, the characteristic specifies an activity that a user of the device is currently performing and the historical content depicts an activity being performed by an action-performing element. In some implementations, the user interest value is determined to have a value that is greater than the threshold interest value in response to the activity that the user is performing an action matching the activity being performed by the action-performing element. As an example, the historical content depicts a person playing polo. In this example, when the device detects that the user is playing polo, the device automatically captures and stores an image of the user playing polo. Referring to FIG. 2, the user interest determiner 220 determines the user interest value 222 based on a comparison of the user activity 140d and the past activities 160d.

As represented by block 330f, in some implementations, the characteristic indicates whether or not a user of the device can provide a user input that corresponds to a request to store the image. In some implementations, the method 300 includes storing the image in response to user interest value being greater than the threshold interest value and the contextual data indicating that the user is unable to provide the user input that corresponds to the request to store the image. For example, the device can automatically capture and store an image when the device detects that the user's hands are occupied, for example, because the user is playing golf or holding a physical article with both his/her hands.

As represented by block 330g, in some implementations, the method 300 includes, in response to the user interest value being less than the threshold interest value, discarding the image after a threshold amount of time has elapsed since the image was captured. For example, as indicated by the cross 192 in FIG. 1E, the electronic device 20 discards the image 28 (e.g., does not store the image 28) in response to the user interest value 190 being less than the threshold interest value 180.

As represented by block 330h, in some implementations, the threshold interest value is a function of the historical content. As such, in some implementations, the method 300 includes determining the threshold interest value based on the historical content. For example, as described in relation to FIG. 2, the threshold interest determiner 230 determines the threshold interest value 180 based on the historical content 160. As described in relation to FIG. 2, in some implementations, the threshold interest value indicates types of locations that the user is interested in (e.g., museums, parks, cities, etc.). In some implementations, the threshold interest value indicates times of day when the user appears to be more interested in capturing images (e.g., mornings, afternoons, evenings, etc.). In some implementations, the threshold interest value indicates types of physical articles that the user is interested in capturing an image of (e.g., natural landmarks such as mountains, or human-made landmarks such as buildings).

In some implementations, storing the image includes capturing the image via the image sensor. In some implementations, storing the image includes storing the image in a local storage at the device. In some implementations, storing the image includes storing the image in a remote storage at another device (e.g., at a server or a cloud computing platform). In some implementations, storing the image include storing the image in a video streaming buffer from where the device subsequently retrieves the image to transmit the image as a part of a video stream.

Figure 4:
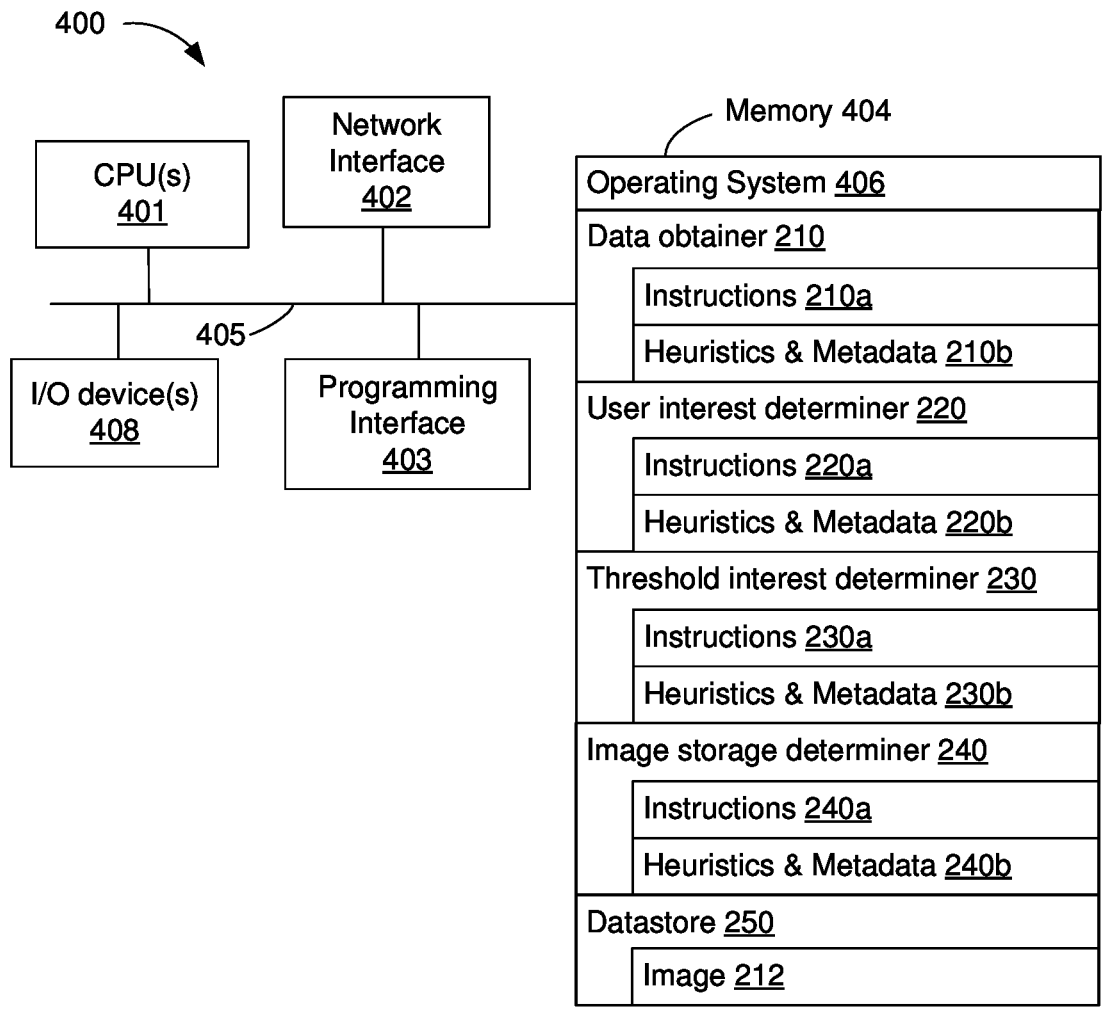
FIG. 4 is a block diagram of a device that captures and stores an image of a physical environment in accordance with some implementations.

FIG. 4 is a block diagram of a device 400 in accordance with some implementations. In some implementations, the device 400 implements the electronic device 20 shown in FIGS. 1A-1E and/or the system 200 shown in FIG. 2. While certain specific features are illustrated, those of ordinary skill in the art will appreciate from the present disclosure that various other features have not been illustrated for the sake of brevity, and so as not to obscure more pertinent aspects of the implementations disclosed herein. To that end, as a non-limiting example, in some implementations the device 400 includes one or more processing units (CPUs) 401, a network interface 402, a programming interface 403, a memory 404, one or more input/output (I/O) devices 408, and one or more communication buses 405 for interconnecting these and various other components.

In some implementations, the network interface 402 is provided to, among other uses, establish and maintain a metadata tunnel between a cloud hosted network management system and at least one private network including one or more compliant devices. In some implementations, the one or more communication buses 405 include circuitry that interconnects and controls communications between system components. The memory 404 includes high-speed random access memory, such as DRAM, SRAM, DDR RAM or other random access solid state memory devices, and may include non-volatile memory, such as one or more magnetic disk storage devices, optical disk storage devices, flash memory devices, or other non-volatile solid state storage devices. The memory 404 optionally includes one or more storage devices remotely located from the one or more CPUs 401. The memory 304 comprises a non-transitory computer readable storage medium.

In some implementations, the memory 404 or the non-transitory computer readable storage medium of the memory 404 stores the following programs, modules and data structures, or a subset thereof including an optional operating system 406, the data obtainer 210, the user interest determiner 220, the threshold interest determiner 230, the image storage determiner 240 and the datastore 250. In various implementations, the device 400 performs the method 300 shown in FIG. 3.

In some implementations, the data obtainer 210 includes instructions 210a, and heuristics and metadata 210b for obtaining the contextual data 140 and the historical content 160 shown in FIGS. 1B-2. In some implementations, the data obtainer 210 performs at least some of the operation(s) represented by block 310 in FIG. 3.

In some implementations, the user interest determiner 220 includes instructions 220a, and heuristics and metadata 220b for determining the user interest value 170 shown in FIGS. 1B-1D, the user interest value 190 shown in FIG. 1E and/or the user interest value 222 shown in FIG. 2. In some implementations, the user interest determiner 220 performs at least some of the operation(s) represented by block 320 in FIG. 3.

In some implementations, the threshold interest determiner 230 includes instructions 230a, and heuristics and metadata 230b for determining the threshold interest value 180 shown in FIGS. 1B-2. In some implementations, the user interest determiner 220 performs at least some of the operation(s) represented by blocks 320 and 330h in FIG. 3.

In some implementations, the image storage determiner 240 includes instructions 240a, and heuristics and metadata 240b for determining whether or not to automatically store the image 212 in the datastore 250. In some implementations, the image storage determiner 240 performs at least some of the operation(s) represented by block 330 in FIG. 3.

In some implementations, the one or more I/O devices 408 include an input device for obtaining an input. In some implementations, the input device includes a touchscreen (e.g., for detecting tap inputs), an image sensor (e.g., for detecting gesture inputs) and/or a microphone (e.g., for detecting voice inputs). In some implementations, the one or more I/O devices 408 include an image sensor (e.g., a scene-facing camera) for capturing images of a physical environment (e.g., for capturing the image 28 shown in FIGS. 1A-2 and/or the image 212 shown in FIG. 2). In some implementations, the one or more I/O devices 408 include a display for presenting a representation of the physical environment.

In various implementations, the one or more I/O devices 408 include a video pass-through display which displays at least a portion of a physical environment surrounding the device 400 as an image captured by a camera. In various implementations, the one or more I/O devices 408 include an optical see-through display which is at least partially transparent and passes light emitted by or reflected off the physical environment.

It will be appreciated that FIG. 4 is intended as a functional description of the various features which may be present in a particular implementation as opposed to a structural schematic of the implementations described herein. As recognized by those of ordinary skill in the art, items shown separately could be combined and some items could be separated. For example, some functional blocks shown separately in FIG. 4 could be implemented as a single block, and the various functions of single functional blocks could be implemented by one or more functional blocks in various implementations. The actual number of blocks and the division of particular functions and how features are allocated among them will vary from one implementation to another and, in some implementations, depends in part on the particular combination of hardware, software, and/or firmware chosen for a particular implementation.

Various processes defined herein consider the option of obtaining and utilizing a user's personal information. For example, such personal information may be utilized in order to provide an improved privacy screen on an electronic device. However, to the extent such personal information is collected, such information should be obtained with the user's informed consent. As described herein, the user should have knowledge of and control over the use of their personal information.

Personal information will be utilized by appropriate parties only for legitimate and reasonable purposes. Those parties utilizing such information will adhere to privacy policies and practices that are at least in accordance with appropriate laws and regulations. In addition, such policies are to be well-established, user-accessible, and recognized as in compliance with or above governmental/industry standards. Moreover, these parties will not distribute, sell, or otherwise share such information outside of any reasonable and legitimate purposes.

Users may, however, limit the degree to which such parties may access or otherwise obtain personal information. For instance, settings or other preferences may be adjusted such that users can decide whether their personal information can be accessed by various entities. Furthermore, while some features defined herein are described in the context of using personal information, various aspects of these features can be implemented without the need to use such information. As an example, if user preferences, account names, and/or location history are gathered, this information can be obscured or otherwise generalized such that the information does not identify the respective user.

While various aspects of implementations within the scope of the appended claims are described above, it should be apparent that the various features of implementations described above may be embodied in a wide variety of forms and that any specific structure and/or function described above is merely illustrative. Based on the present disclosure one skilled in the art should appreciate that an aspect described herein may be implemented independently of any other aspects and that two or more of these aspects may be combined in various ways. For example, an apparatus may be implemented and/or a method may be practiced using any number of the aspects set forth herein. In addition, such an apparatus may be implemented and/or such a method may be practiced using other structure and/or functionality in addition to or other than one or more of the aspects set forth herein.

What is claimed is:

1. A method comprising:
   at a device including a display, an image sensor, a non-transitory memory and one or more processors coupled with the display, the image sensor and the non-transitory memory:
   while presenting a representation of a physical environment of the device:
   obtaining contextual data that indicates a characteristic of the physical environment, the device or a user of the device; and
   obtaining an indication of historical content associated with the device;
   determining, based on the characteristic indicated by the contextual data and the historical content, a user interest value that indicates a user interest level in the physical environment; and
   storing an image captured by the image sensor in response to the user interest value being greater than a threshold interest value.

2. The method of claim 1, wherein the contextual data comprises the image captured by the image sensor and the historical content comprises previous images captured by the image sensor or presented by the device;
   wherein determining the user interest value comprises determining a similarity score that indicates a degree of similarity between the image captured by the image sensor and the previous images; and
   wherein the user interest value is determined to have a value that is greater than the threshold interest value in response to the similarity score being greater than a threshold similarity score.

3. The method of claim 2, wherein the image captured by the image sensor includes a two-dimensional representation of a physical article in the physical environment; and
   wherein the similarity score indicates a degree of similarity between the physical article in the physical environment and an object depicted in at least one of the previous images.

4. The method of claim 1, wherein the historical content comprises a browsing history or a search history of the device;
   wherein determining the user interest value comprises determining a relevance score that indicates a relevance of the physical environment to the browsing history or the search history of the device; and
wherein the user interest value is determined to have a value that is greater than the threshold interest value in response to the relevance score being greater than a threshold relevance score.

5. The method of claim 4, wherein the relevance score indicates whether or not a physical article in the physical environment is within a similarity threshold of an object related to the browsing history or the search history.

6. The method of claim 1, wherein the historical content comprises media content items that the device has presented within a recency threshold;
wherein determining the user interest value comprises determining a relevance score that indicates a relevance of the physical environment to the media content items; and
wherein the user interest value is determined to have a value that is greater than the threshold interest value in response to the relevance score being greater than a threshold relevance score.

7. The method of claim 6, wherein the relevance score indicates whether the physical environment matches an environment depicted in at least one of the media content items.

8. The method of claim 1, wherein the characteristic comprises a physiological measurement;
wherein determining the user interest value comprises determining whether the physiological measurement satisfies a physiological threshold; and
wherein the user interest value is determined to have a value that is greater than the threshold interest value in response to the physiological measurement satisfying the physiological threshold.

9. The method of claim 8, wherein the physiological measurement comprises a heart rate value and the physiological threshold comprises a threshold heart rate value; and
wherein the user interest value is determined to have a value that is greater than the threshold interest value in response to the heart rate value being greater than the threshold heart rate value.

10. The method of claim 8, wherein the physiological measurement comprises a perspiration rate value and the physiological threshold comprises a threshold perspiration rate value; and
wherein the user interest value is determined to have a value that is greater than the threshold interest value in response to the perspiration rate value being greater than the threshold perspiration rate value.

11. The method of claim 8, wherein the physiological measurement comprises a gaze vector that indicates a gaze position, a gaze intensity or a gaze duration of a user of the device, and the physiological threshold comprises a threshold time duration; and
wherein the user interest value is determined to have a value that is greater than the threshold interest value in response to the gaze position corresponding to a particular physical article in the physical environment for the threshold time duration.

12. The method of claim 8, wherein the physiological measurement comprises a facial expression of a user of the device and the physiological threshold comprises a threshold facial expression; and
wherein the user interest value is determined to have a value that is greater than the threshold interest value in response to the facial expression matching the threshold facial expression.

13. The method of claim 8, wherein the physiological measurement comprises a voice characteristic associated with an utterance of a user of the device and the physiological threshold comprises a threshold voice characteristic; and
wherein the user interest value is determined to have a value that is greater than the threshold interest value in response to the voice characteristic satisfying the threshold voice characteristic.

14. The method of claim 1, wherein the characteristic specifies an activity that a user of the device is currently performing and the historical content depicts an activity being performed by an action-performing element; and
wherein the user interest value is determined to have a value that is greater than the threshold interest value in response to the activity that the user is performing matching the activity being performed by the action-performing element.

15. The method of claim 1, wherein the characteristic indicates whether or not a user of the device can provide a user input that corresponds to a request to store the image; and
wherein storing the image comprises storing the image in response to the user interest value being greater than the threshold interest value and the contextual data indicating that the user is unable to provide the user input that corresponds to the request to store the image.

16. The method of claim 1, further comprising:
in response to the user interest value being less than the threshold interest value, discarding the image after a threshold amount of time has elapsed since the image was captured.

17. The method of claim 1, wherein presenting the representation of the physical environment comprises:
capturing the image via the image sensor; and
displaying the image on the display.

18. The method of claim 1, wherein the display comprises an optical see-through display; and
wherein presenting the representation of the physical environment comprises presenting an optical see-through of the physical environment by allowing visible light from the physical environment to enter eyes of a user of the device via the optical see-through display.

19. A device comprising:
one or more processors;
an image sensor;
a display;
a non-transitory memory; and
one or more programs stored in the non-transitory memory, which, when executed by the one or more processors, cause the device to:
while presenting a representation of a physical environment of the device:
obtain contextual data that indicates a characteristic of the physical environment, the device or a user of the device; and
obtain an indication of historical content associated with the device;
determine, based on the characteristic indicated by the contextual data and the historical content, a user interest value that indicates a user interest level in the physical environment; and store an image captured by the image sensor in response to the user interest value being greater than a threshold interest value.

20. A non-transitory memory storing one or more programs, which, when executed by one or more processors of a device including a display and an image sensor, cause the device to:
  while presenting a representation of a physical environment of the device:
    obtain contextual data that indicates a characteristic of the physical environment, the device or a user of the device; and
    obtain an indication of historical content associated with the device;
  determine, based on the characteristic indicated by the contextual data and the historical content, a user interest value that indicates a user interest level in the physical environment; and
  store an image captured by the image sensor in response to the user interest value being greater than a threshold interest value.

* * * * *